United States Patent
Malcolm et al.

(10) Patent No.: US 6,895,969 B2
(45) Date of Patent: May 24, 2005

(54) ORTHOPEDIC TRACTION DEVICE

(75) Inventors: Roger J. Malcolm, 970 B Calle Amanecer, San Clemente, CA (US) 92673; Tim M. Salter, Silverado, CA (US); Rob D. Kelly, Anaheim, CA (US); Ward L. Sanders, Edinboro, PA (US); Bryan P. Peterson, San Clemente, CA (US)

(73) Assignee: Roger J. Malcolm, San Clemente, CA (US)

( * ) Notice: Subject to any disclaimer, the term of this patent is extended or adjusted under 35 U.S.C. 154(b) by 0 days.

(21) Appl. No.: 10/361,145

(22) Filed: Feb. 6, 2003

(65) Prior Publication Data

US 2004/0154627 A1 Aug. 12, 2004

(51) Int. Cl.⁷ .............................................. A61G 15/00
(52) U.S. Cl. ...................... 128/845; 128/846; 128/869; 602/32; 602/36
(58) Field of Search ................................ 128/845, 846, 128/869, 870, 882, 878; 602/32, 33, 35, 36, 38; 5/621, 623, 624

(56) References Cited

U.S. PATENT DOCUMENTS

| | | | | |
|---|---|---|---|---|
| 3,662,750 A | * | 5/1972 | Jorgensen | 602/35 |
| 4,024,860 A | * | 5/1977 | Chelnokov et al. | 602/32 |
| 4,872,656 A | * | 10/1989 | Brendgord et al. | 5/624 |
| 4,964,400 A | * | 10/1990 | Laico et al. | 128/878 |
| 5,195,947 A | * | 3/1993 | Bode | 602/32 |
| 5,290,220 A | * | 3/1994 | Guhl | 128/882 |
| 5,658,315 A | * | 8/1997 | Lamb et al. | 602/32 |
| 5,667,461 A | * | 9/1997 | Hall | 602/36 |
| 5,807,294 A | * | 9/1998 | Cawley et al. | 602/32 |
| 5,957,135 A | * | 9/1999 | Molina | 128/845 |

* cited by examiner

Primary Examiner—Fadi H. Dahbour
(74) Attorney, Agent, or Firm—Henri J. A. Charmasson; John D. Buchaca

(57) ABSTRACT

An orthopedic traction apparatus includes in coaxial arrangement, a first tubular member anchored to a operating table or other stationary structure supporting a patient, and a second tubular member telescopically moving within the first one. A hand-crank and jack-screw mechanism is used to vary the position of the second member in relation to the first member. A tensiometer is provided at the distal end of the second member proximate a fixture adapted for attachment to a part of a patient's body. The tensiometer is based on a compressible, calibrated coil spring and is provided with a vernier scale for convenient and precise adjustment of the traction force. Alternately, the tensiometer uses a load-cell driving a digital read-out.

12 Claims, 5 Drawing Sheets

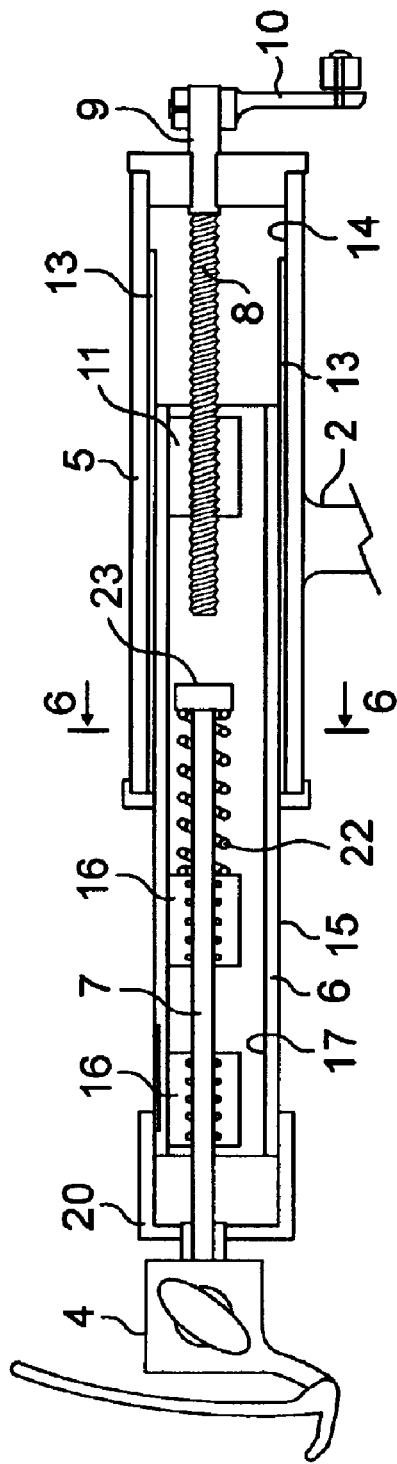
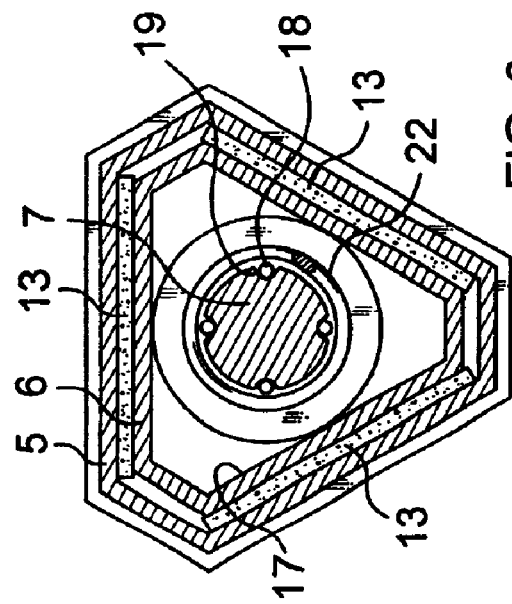
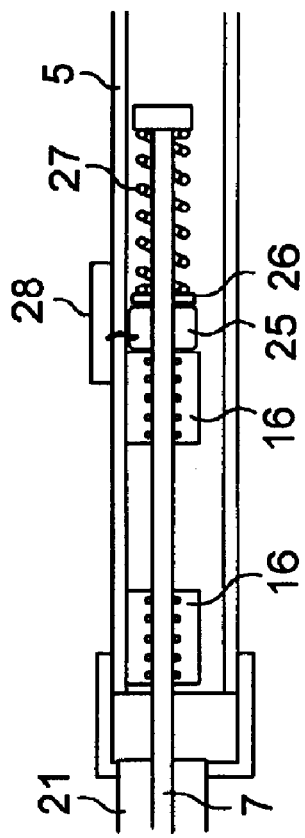
FIG. 4
FIG. 5
FIG. 6

ORTHOPEDIC TRACTION DEVICE

FIELD OF THE INVENTION

This invention relates to orthopedic equipment and more particularly to mechanisms used by orthopedic surgeons and physical therapists to apply traction to a limb or other part of the body.

BACKGROUND OF THE INVENTION

Orthopedic surgeons and physical therapists often use traction to treat traumas affecting a part of body's bone structure.

For instance, traction may be applied to a leg in order to realign a broken femur bringing the two fractioned interfaces together so that they can be rejoined. Traction may also be used to lengthen a limb that has atrophied as a result of a degenerative muscular disorder such as poliomyelitis. In such a case, the femur is sewed into two sections and traction is applied to the leg to bring the two severed sections into close proximity and letting the natural regrowth of the bone feel the traction-induced gap.

Traction is typically applied over a long period of time with progressive increase of the traction force. Accordingly, orthopedic traction requires a careful control of that force. This is commonly achieved by use of weights dangling from a string passing over a pulley and attached at the other end to the patient's limb. Weights can be progressively added or removed to adjust the traction force. An example of this type of traction equipment is disclosed in U.S. Pat. No. 4,653,482 Kurland. This prior art equipment is bulky, heavy, and cumbersome to use. The handling of weights can be hazardous and their mass requires very sturdy operating tables and other supporting jigs.

The instant invention results from an attempt to eliminate the use of weights-biased orthopedic traction devices.

SUMMARY OF THE INVENTION

The principal and secondary objects of this invention are to provide an orthopedic traction apparatus that can be conveniently installed on a surgery table, treatment jig, or hospital bed and provide an accurate indication of the traction force while avoiding the use of weights and other heavy and cumbersome components. These and other valuable objects are achieved by an orthopedic traction apparatus which utilizes a jackscrew mechanism packaged in a compact tubular enclosure that incorporates a tensiometer and is made of sturdy yet light weight carbon fiber material. The apparatus is engineered to minimize friction between the moving components while maintaining their stability.

BRIEF DESCRIPTION OF THE DRAWING

FIG. 4 is a cross-sectional view of the apparatus;

FIG. 5 is a cross-sectional view of the load-cell tensiometer;

FIG. 6 is a cross-sectional view taken along line 6—6 of FIG. 4; and

DESCRIPTION OF THE PREFERRED EMBODIMENT OF THE INVENTION

Figure 1:
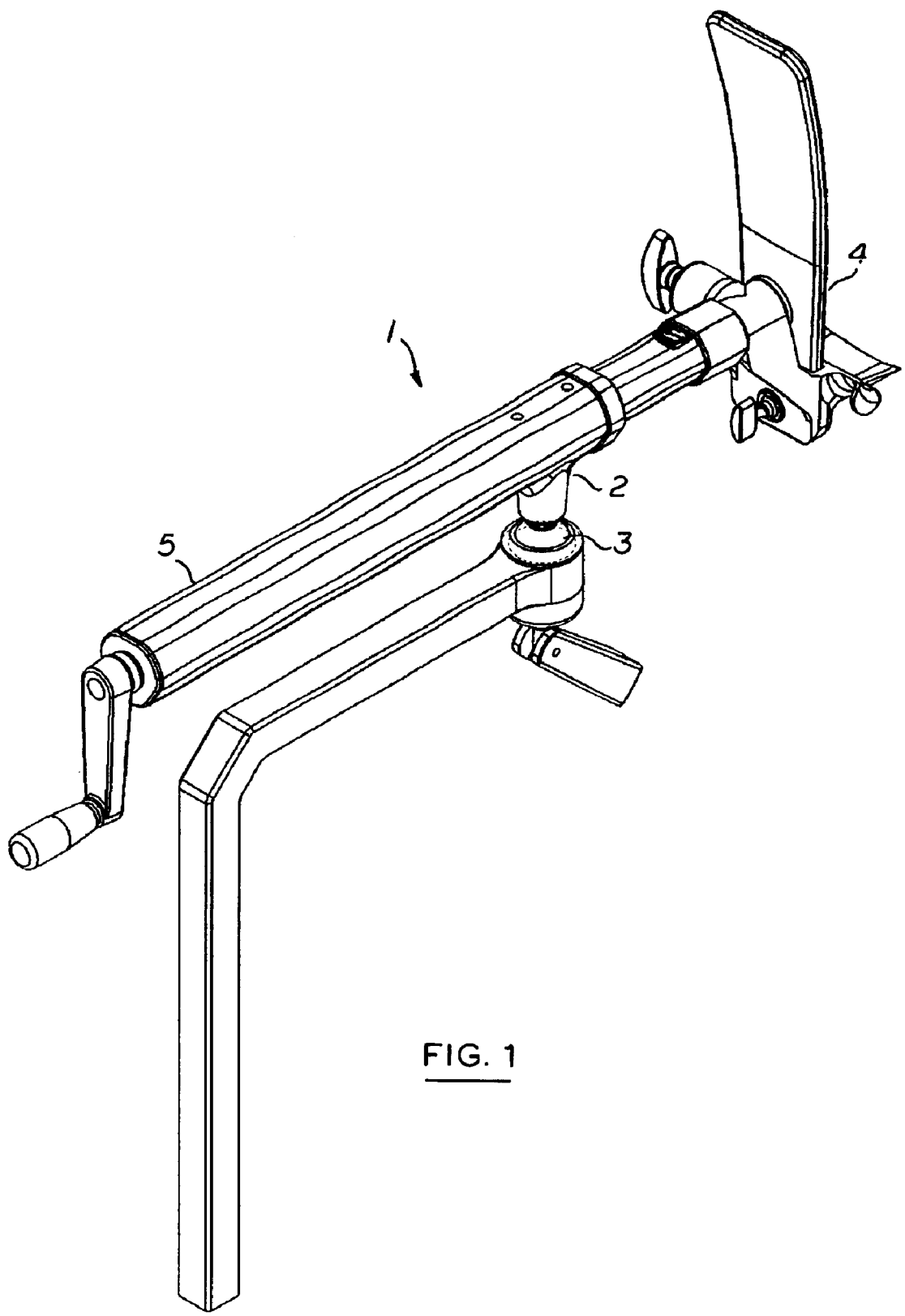
FIG. 1 is a perspective view of the traction apparatus.

Referring now to the drawing, there is shown an orthopedic apparatus 1 for applying traction to a patient's body part and more specifically to a patient's arm or leg. The apparatus preferably anchored to an operating table, bed, treatment jig or other stationary structure fixedly supporing the pateint. The attachment is by means of a multi-positonable coupling comprising a bracket 2 terminated by a ball-and-socket assembly 3. At the distal end of the apparatus a a stirrup fixture 4 is configured to securely attach to a boot worn by the patient. Typically, a pair of such traction apparatus would be used to operate on both legs in order to balance the tension applied to the patient's pelvis. The traction mechanism is contained into a first tubular housing 5 secured to the coupling bracket 2 and a more distal second tubular housing 6 concentrically and telescopically engaged into the first.

The stirrup fixture 4 is mounted at the distal end of a spline shaft 7 slidingly engaged into the distal end of the second tubular housing 6. Accordingly, the spline shaft, second and first housings are co-axially engaged or co-nested as more specifically illustrated in FIG. 6. A drive screw 8 axially mounted inside the first housing 5 has a protruding proximate tip 9 protruding from the proximal end of the first housing. A handle 10 or hand-knob is attached to the proximal tip to form a hand-crank mechanism. The opposite distal end of the drive screw is engaged in the threaded channel of the body 11 such as a nut captured within a proximal region of the second housing. It, thus, can be understood that the axial position of the second housing in relation to the first housing can be translated by manipulating the handle in either direction. A tansionmeter 12 is interposed between the second housing 6 and the spline shaft 7 as explained below.

The first tubular housing 5 has a polygonal cross-section whose inner periphery, although slightly larger, substantially matches the outer periphery of the second housing 6. In order to assure a stable movement and limit the friction between the two tubular housings, elongated rectangular glide pads 13 are positioned between overlapping portions of the inner wall surface 14 of the first housing and outer wall surface 15 of the second housing. Similarly, in order to assure a stable and low-friction axial movement of the spline shaft 7 within the second housing, the shaft is centrally supported by two or more ball-bearing, bushings 16.

Each ball-bearing bushing is fixedly secured about its outer periphery to the inner wall surface 17 of the second housing so that the bushing is not allowed any axial or rotational movement in relation to the housing. The central bore of the bushing is lined with rotating bearing balls 18 which engage longitudinal grooves 19 in the spline shaft 7. The balls circulate within oval channels (not shown) to assure a smooth and quasi-frictionless axial movement of the shaft while maintaining its stability within the housing. this type of bushing is commercially available and is well known to those skilled in mechanical arts.

Figure 2:
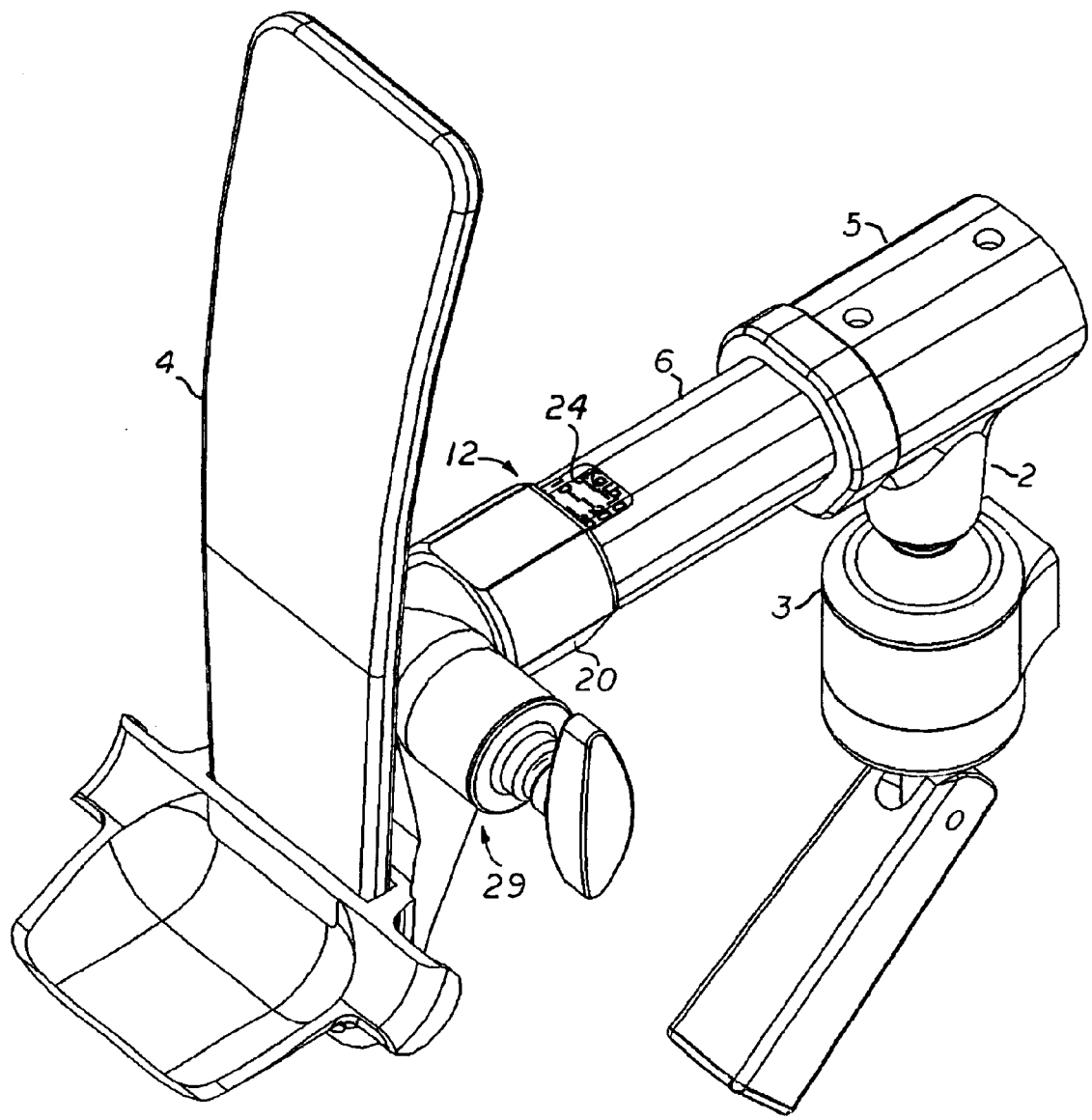
FIG. 2 is a perspective view of the distal portion thereof.
Figure 3:
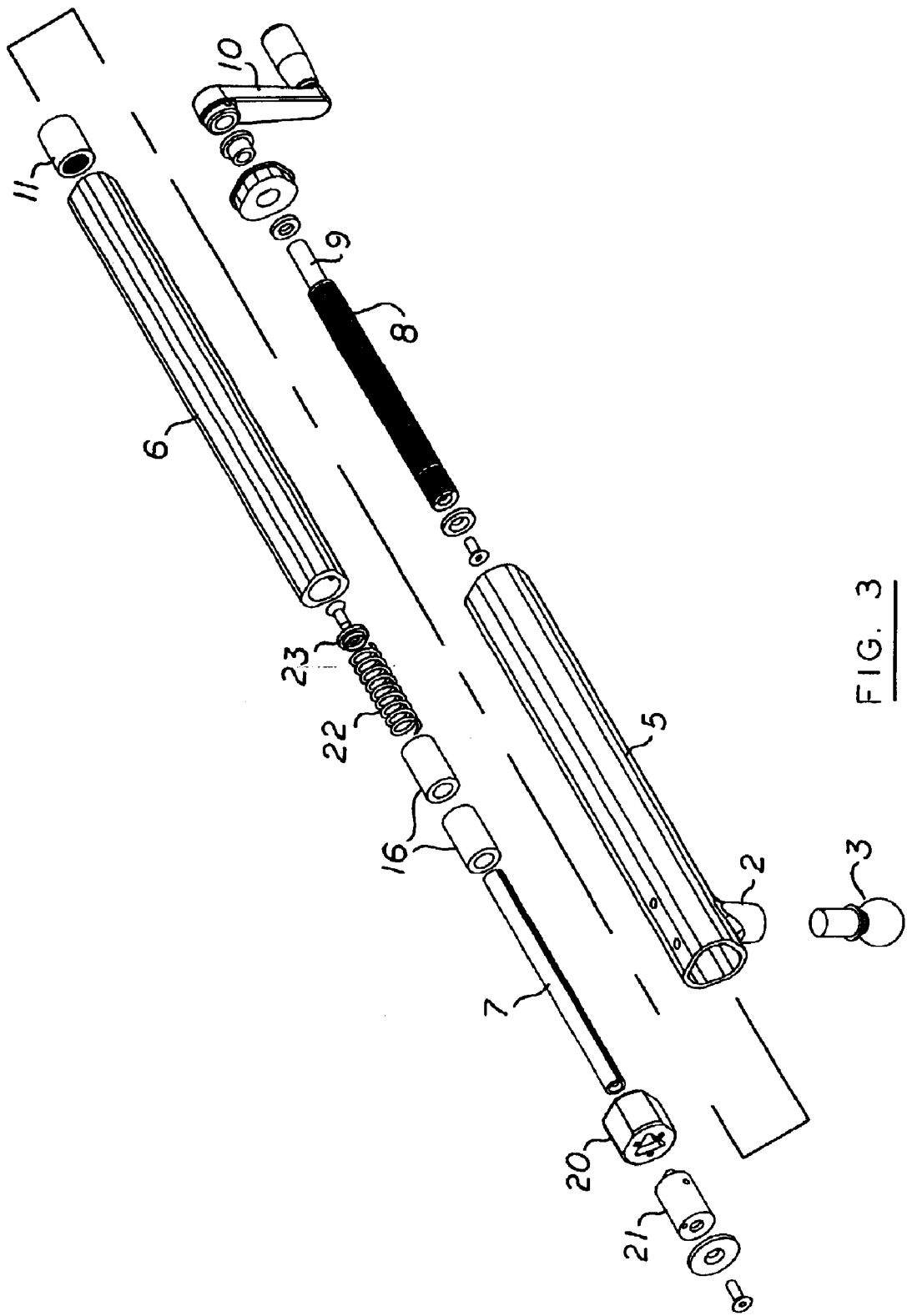
FIG. 3 is an exploded perspective view of some of the components.

As illustrated in FIG. 2, the tensiometer 12 comprises a cap 20 that slidingly closes the distal end of the second tubular housing 6 and is fixedly secured to the spline shaft by a coupling cylindrical 21. A calibrated coil spring 22 is engaged upon the spline shaft between the most proximal one of the bushings 16 fixedly secured to the inner wall of the second housing and a flange 23 radially projecting from the proximal end of the spline shaft. A vernier scale 24, preferably made in contrasting colors, is engraved in the distal section of the second housing that is overlapped by the cap 20. The scale is graduated so that, as the spline moves, the edge of the cap indicates the amount of traction force applied to the calibrated spring by the tension between the spline shaft and the first and secnd housings.

In an alternate embodiment of the tensionmeter illustrated in FIG. 5, a load-cell 25 backed up by a washer 26 and a non-calibrated coil spring 27 is used in lieu of the calibrated coil spring. The output of the load-cell is fed to an electronic digital read-out 28 mounted on the first enclosure. The load-cell and read-out are powered by a battery (not shown) contained in the read-out enclosure.

Figure 7:
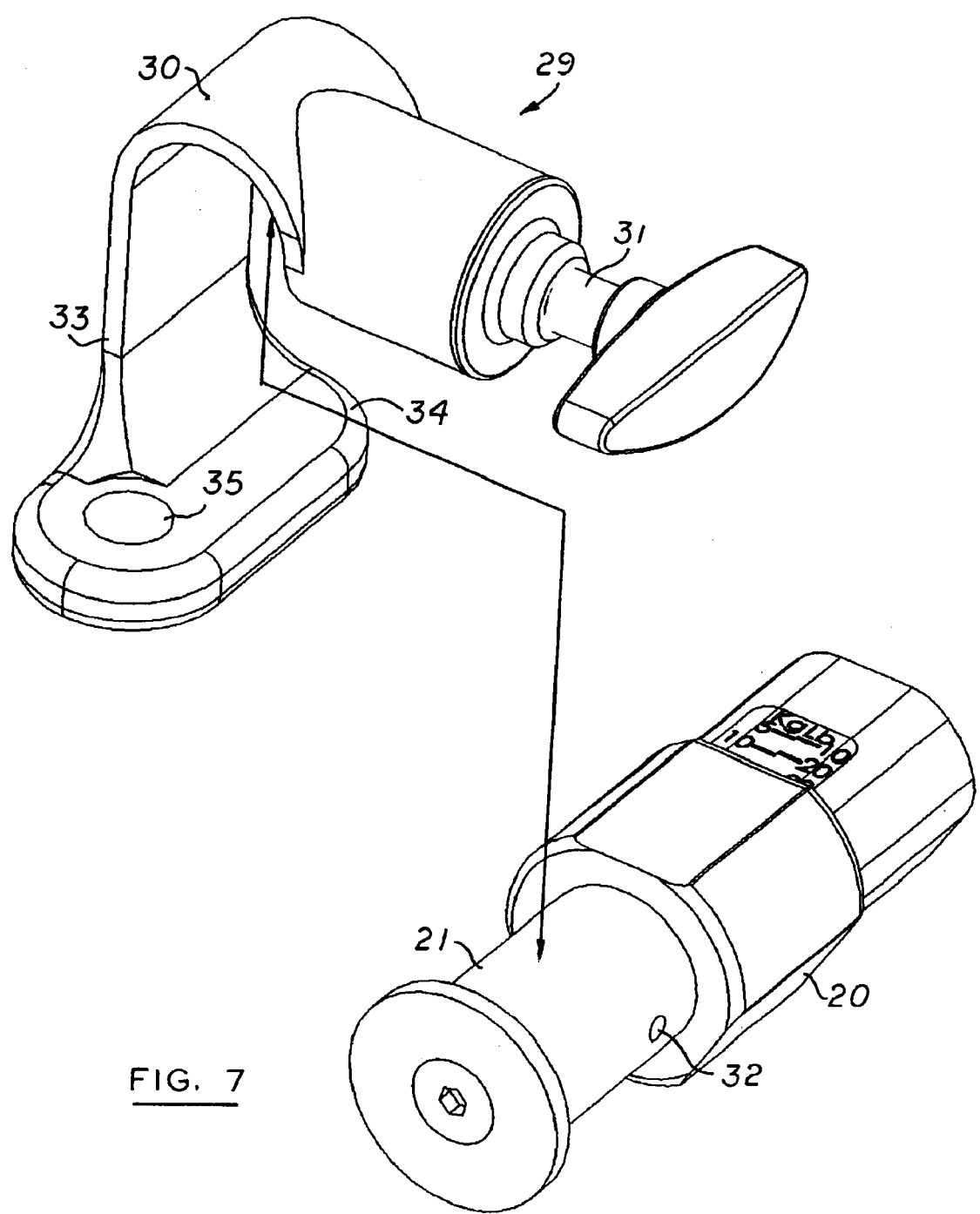
FIG. 7 is an exploded perspective view of the attachment mechanism for the patient's fixture.

As more specifically illustrated in FIG. 7, a clamping bracket 29 is positioned between the coupling 21 at the distal end of the spline shaft and the stirrup fixture 4 attachable to a patient's boot. The clamping bracket has a vaulted section 30 that intimately fit over the coupling 21. A knob-driven tightening screw 31 is used to fixedly secure the bracket. The tip of the screw (not shown in the drawing) penetrates a small depression 32 on the surface of the coupling to prevent rotation of the bracket about the coupling. The shank 33 of the bracket supports a foot 34 having a circular hole 35 bored substantially perpendicular to the coupling and spline shaft 7. This hole is sized to receive a post associated with the stirrup fixture. The hole can alternately receive the shank of a hook attachable to another type of fixture worn by a patient. The foot 34 can also be replaced by a block having one or more holes positioned and dimensioned to accept a variety of attachment hardware.

The apparatus is preferably made strong but lighweight carbon fiber material. The narrow pitch of the drive screw and drive nut assures a slow, stable and precise adjustment of the tension which, typically, does not extend over more than 3 or 4 centimeters and in a range of 0.5 to 40 kilograms.

While the preferred embodiment of the invention has been described, modifications can be made and other embodiments may be devised without departing from the spirit of the invention and the scope of the appended claims.

What is claimed is:

1. An apparatus, for applying traction to a patient's body part which comprises:
   a first tubular housing;
   a second tubular housing telescopically engaging said first housing;
   a drive-screw rotatably mounted within one of said housings;
   an unrotatable and axially translatable body having a threaded channel engaged by said drive-screw, said body being shaped, dimensioned and positioned to axially translate the other one of said housings;
   a fixture attachable to said body part; and
   a tensiometer axially linking said fixture to said other one of said housings.

2. The apparatus of claim 1, wherein said second housing comprises a drive-nut having said threaded channel.

3. The apparatus of claim 2, wherein said first housing has an inner wall having a polygonal cross-section, and said second housing has an outer wall surface substantially matching said inner wall.

4. The apparatus of claim 3, which further comprises a plurality of rectangular glide-pads positioned between overlapping portions of said inner and outer walls.

5. The apparatus of claim 2 which further comprises means for anchoring said first housing to a structure supporting said patient.

6. The apparatus of claim 3, wherein said drive-nut is fixedly attached to said second housing.

7. The apparatus of claim 1 which further comprises a hand-crank coupled to one of said drive-screw and body.

8. The apparatus of claim 1, wherein said fixture comprises a shaft partially and axially engaged in to said other one of said housings; and
   said tensiometer comprises a calibrated coil spring connected to said shaft and to said other one of said housings; and
   a vernier scale positioned to indicate the displacement of said shaft in relation to said other one of said housings.

9. The apparatus of claim 8 which further comprises at least one axial ball bearing supporting said shaft within said other one of said housings.

10. The apparatus of claim 9, wherein sections of each said shaft, second housing and first housing are coaxially co-nested.

11. The apparatus of claim 8 which further comprises a cylindrical coupling mounted at the end of said shaft;
   a clamping bracket removably secured over said coupling and having a hole positioned and dimensioned to receive said fixture.

12. The apparatus of claim 1, wherein said fixture comprises a shaft partially and axially engaged into said other one of said housings; and
   said tensiometer comprises a load-cell connected to said shaft and generating a signal, and to said other one of said housings and a digital read-out driven by said signal.

* * * * *